United States Patent
Oko et al.

(10) Patent No.: US 6,428,773 B1
(45) Date of Patent: Aug. 6, 2002

(54) SHADOW-EFFECT COSMETIC COMPOSITION

(75) Inventors: Jennifer Oko, Stony Brook; Isaac D. Cohen, Brooklyn, both of NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/482,586

(22) Filed: Jan. 13, 2000

(51) Int. Cl.$^7$ .................. A61K 7/021; A61K 7/025; A61K 9/14; C04B 14/20; C09C 1/36

(52) U.S. Cl. .................. 424/63; 106/415; 106/417; 106/418; 106/436; 106/459; 424/64; 424/401; 424/489

(58) Field of Search .................. 424/401, 489, 424/63, 64; 106/415, 417, 418, 436, 459

(56) References Cited

U.S. PATENT DOCUMENTS

| | | | | |
|---|---|---|---|---|
| 4,744,832 A | * | 5/1988 | Franz et al. | 106/309 |
| 5,082,660 A | | 1/1992 | Ounanian et al. | |
| 5,690,916 A | | 11/1997 | Kimura et al. | |
| 6,117,435 A | * | 5/2000 | Painter et al. | 424/401 |

FOREIGN PATENT DOCUMENTS

WO    WO 99/66883    12/1999

OTHER PUBLICATIONS

Nishikata, K., et al., "A Natural–Looking Makeup", Cosmetics & Toiletries, No. 112, Jan.–Jun. 1997, pp. 39–56.

Product brochure, Presperse, Inc., 4 pages, received Apr. 1999.

* cited by examiner

Primary Examiner—Jose' G. Dees
Assistant Examiner—Marina Lamm
(74) Attorney, Agent, or Firm—Karen A. Lowney, Esq.

(57) ABSTRACT

The invention relates to a cosmetic composition, containing a four-layered interference pigment comprising an innermost layer of mica, a first outer layer of a colored pigment, a second outer transparent layer, and an outermost layer of a colored pigment, combined with a traditional interference pigment. The compositions, when applied to a facial or body surface, emphasize the contours of the surface, creating greater depth and dimension. The compositions are particularly useful as lip products, to create a fuller, plumper look to the lips.

19 Claims, No Drawings

SHADOW-EFFECT COSMETIC COMPOSITION

FIELD OF THE INVENTION

The present invention relates to cosmetic compositions. More specifically, the invention relates to cosmetic compositions that can provide a shadowing effect that emphasizes the contours of the lips and other facial features.

BACKGROUND OF THE INVENTION

The purpose of most cosmetics is to enhance the appearance of facial or body features. To extreme cases, the cosmetic acts to completely cover or eliminate from the sight of the casual observer a feature that the user considers unattractive, for example, concealment of dark shadows under the eyes, so as to enhance the overall appearance of the eyes. In other cases, however, the cosmetic is intended to cause a particular feature to become noticeable. The practice of emphasizing facial features, in particular by bright coloration, goes back several thousand years, when it was common to add powdered colored ores, such as red ochre(iron oxide) directly to the face to color the cheeks, or kohl(galena, a lead ore) to line the eyes.

The art of cosmetics has advanced significantly since prehistoric times. While the purpose is largely still enhancement, the trend is toward a more natural look, and emphasizing good features with more subtle strategies. To this end, a considerable focus has been devoted to development of cosmetics with unusual optical effects, i.e., that persuade the observer's eye to see a more perfect image of the face, e.g., one having no lines or blemishes, than actually exists, without the use of large quantities of heavy opaque pigments to cover flaws. Examples of cosmetics said to achieve such an effect are described for example in Nishikata et al., Cosmetics and Toiletries 112: 39–55, 1997; U.S. Pat. Nos. 5,690,916, and 5,082,660; and PCT US99/13240.

An extension of this approach is to make more or less prominent a particular feature that does not comport with the perceived ideal appearance of that feature. It has been common for many years for cosmetics users to "contour" a feature by the application of two different shades of makeup, one light, one darker, to a less than perfect facial feature. The light makeup is placed on the area to be highlighted and the darker makeup placed on the area to be de-emphasized, resulting in a shadowing effect that can make the feature, for example cheekbones, appear more dimensional than they would ordinarily appear. This approach, however, typically also relies on the use of traditional heavily pigmented makeup, and necessarily requires the use of two different makeup products and considerable skill on the part of the user.

There thus continues to be a need for a cosmetic product that will allow the user to contour various features of the face, or other parts of the body, to emphasize or create the appearance of dimension and depth where it does not naturally occur. The present invention now provides such a product.

SUMMARY OF THE INVENTION

The invention provides a cosmetic composition, containing a four-layered interference pigment comprising an innermost layer of mica, a first outer layer of a colored pigment, a second outer transparent layer, and an outermost layer of a colored pigment, combined with a traditional interference pigment. The composition, when applied to various skin surfaces, and particularly the lips, creates a shadow effect which in effect serves to highlight one portion of the treated surface. Thus, for example, when applied to lips, it can make the prominent portions of the lips appear fuller by shadowing the less prominent portion of the lip.

DETAILED DESCRIPTION OF THE INVENTION

The compositions of the invention provide a unique appearance to the skin surface to which they are applied, by highlighting the natural relief of the face and body's contours. An essential feature of the composition is a unique interference platelet having four distinct layers: an inner core of mica, a first outer layer of a colored pigment, a second outer transparent layer, and a third, outermost layer of a colored pigment. Such pigments, hereinafter referred to as a "shadow pigments", are known in the art to provide a "color-flop" effect, which means that, depending on the angle at which the cosmetic containing the pigment is viewed, the viewer will see a different color, which in practical application results in a shift from light to dark, causing a shadowing effect on the treated surface. The shadowing thus emphasizes whatever relief there may be on the treated surface, making an otherwise flat feature appear to have greater dimension.

To the best of Applicants' knowledge, there is only one type of such pigment now publicly available; the commercially available form comprises a mica core, surrounded by a first pigmented red layer comprising a iron oxide, a second layer of transparent silica and an outermost yellow pigmented layer comprising an iron oxide combined with titanium dioxide. The overall effect of this combination is that the pigment appears yellow when viewed at the specular reflection angle, and reddish at other angles of reflection. This combination produces an overall orange-brown color, which is useful when trying to mimic skin color; indeed, the only known previous use of this pigment is for foundations or facial powders. which in use would bring out the relief of the cheekbones, or slenderize the appearance of the nose. Notwithstanding its apparent benefits, however, the color of the material makes it difficult, if not impossible, to create other shades that might also be desirable, for example, pinks or blue-reds, that would be useful in other types of makeup products such as lipsticks or blushes.

What would seem to be an easy solution to this limitation would be to combine the unique interference pigment with other standard pigments, such as additional metallic oxides of different colors, so as to modify or dilute the orange color. However, when this combination is made in amounts sufficient to alter the color accordingly, it has the result of neutralizing the contrast between the two colors of the interference pigment, thereby resulting in a loss of the color-flop effect. Similar disappointing results have also been observed when the shadow pigment is combined with transparent dyes or stains. Thus, to date, the yellow-red pigment has had little practical value beyond its use in facial makeup intended to mimic natural skin color.

It has now been unexpectedly discovered, however, that it is possible to combine the unique interference pigment with one or more standard interference pigments to obtain a variety of different shades, including reds, blues and pinks, without altering the desired light-to-dark shift effect. The resulting compositions can now be used in a variety of different forms, particularly as lipsticks, in order to emphasize the contours of different areas of the face and body, rather than just the cheeks or nose.

Thus, the compositions of the invention comprise the unique shadow pigment in combination with at least one traditional colored interference pigment. Traditional interference pigments, for purposes of the present specification and claims, are defined as thin platelike layered particles having a high refractive index, which, at a certain thickness, produce interference colors, resulting from the interference of typically two, but occasionally more, light reflections, from different layers of the plate, but which do not contain the four-layered arrangement of the shadow pigment. The most common examples of traditional interference pigments are micas layered with about 50–500 nm, films of $TiO_2$, $Fe_2O_3$, or $Cr_2O_3$, or combinations thereof. Such pigments are often pearlescent, and may be uncoated or coated. Coatings include, but are not limited to, silica, nylon or polymethylmethacrylate (PMMA). The interference pigments used in the present invention can have a white base color with a pearlescence that may or may not be colored; alternately, they may have a colored base, with a pearlescence that may or may not be colored. Preferred are interference pigments having a white base with a colored pearlescence. A number of such pigments are commercially available, for example, under the trade names Timiron (Rona) or Flamenco (Englehard). Preferably, to counteract the orange/brown of the preferred shadow pigment, the colored pigment is blue, violet, gold or green, or combinations thereof, although small quantities of other colored interference pigments can also be used. Generally, the interference particle size is from about 1 to about $200\mu$, preferably is about 3 to about $100\mu$, and more preferably is between about 5 to about $50\mu$. In a formulation of the present invention, the standard interference pigment is preferably used in an amount of from about 1–20%, more preferably about 5–15%, by weight of the composition.

The shadow pigment, when used in combination with the standard interference pigment, is present in an amount of from about 1–20%, preferably about 5–15% by weight. In a particularly preferred embodiment, the amounts of shadow pigment and traditional interference pigment are approximately equal. The preferred embodiment of the invention comprises the shadow pigment known as "Color Relief", distributed by Presperse (South Plainfield, N.J.). As noted above, this material is a platelet comprising a core of mica, with a first outer layer of iron oxide, a second outer layer of transparent silica, and an outermost layer of titanium dioxide and iron oxide, which when applied gives a color-flop effect from yellowish to reddish. The preferred ratio of these components is 61:15:9:(14.3+0.7) mica:iron oxide:silica: (titanium dioxide+iron oxide).

Although these components in the designated ratios are preferred, it is possible to employ similar platelets with different pigment components, for example, each pigmented layer can be composed of different pigments, such as different combinations of inorganic pigments, i.e., red, brown, black or yellow iron oxides, titanium dioxide, ferric ammonium ferrocyanide (blue), manganese violet, ultramarine blue, chrome oxide (green), talc, lecithin modified talc, zeolite, kaolin, lecithin modified kaolin, or zinc oxide. Alternately the pigmented layers may comprise organic pigments, such as phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates and stains, such as bromo dyes and fluorescein dyes. It will be understood that a combination of organic and inorganic pigments in the pigmented layers is also possible. Moreover, it is possible to employ a different transparent layer: although silica is particularly preferred for cosmetic purposes, other transparent materials, such as aluminum oxide or magnesium fluoride, can also be used.

Although, as noted above, using standard non-interference pigments individually in the way they are ordinarily used in color cosmetics reduces or eliminates the color shift observed with the shadow pigment, it is possible to incorporate small amounts of pigment grind into the formulation, at much lower levels than would ordinarily be used. Typically, pigment is present in a formulation in an amount of at least about 3 to about 8%. For the present purposes, inorganic pigments, particularly metal oxides, as well as organic pigments, can be used in an amount of up to about 5% total, but more preferably constitute no more than about 1 to about 3% total of the entire product. It is within the skill in the art to adjust the amounts of different pigment types to achieve the desired shade.

The combination of shadow pigment and interference pigment can be added to any type of vehicle ordinarily used in preparing makeup, either liquid, solid, or powder. The combination can be used, for example, in a foundation, blush, lipstick or gloss, bronzer, or eyeshadow, and the combination is incorporated into the formulation in the same way any other pigment component would be added. The combination can also be used in body products, to emphasize the contours of well-developed musculature, such as on the upper arms or thighs.

In a particularly preferred embodiment, the pigment combination is used in a wax-based product, for example, a stick foundation or blush, or preferably, a lipstick, that comprises greater than about 5%, and preferably from 10% to about 30% by weight, of wax. It has been unexpectedly discovered that the incorporation of the novel combination in a wax-based product actually appears to enhance the color shift observed. It is not unknown in the art to create color shift in, for example, a lipstick by incorporation of traditional interference pigments; however, in such cases, the shift in color confers no other effect but that, i.e., there is simply a change in color depending upon the angle of viewing. In contrast, with the combination of the present invention, upon application to the lips, the product creates a shadow effect on the lip surfaces, i.e., a shift from light to dark rather than a simple color shift. The shift from light to dark adds depth and definition to the lips. Consequently, the lips appear plumper and more dimensional at various angles of viewing than with other lip products or without the lipstick at all. In a preferred formulation, the lipstick comprises from about 1 to about 20% of shadow pigment, about 1 to about 20% interference pigment, and less than about 5%, more preferably less than about 3% of traditional pigments(metal oxides and organics), in a standard wax lipstick base.

In connection with the wax base, the term "wax" will be understood to encompass any organic component that is solid at room temperature, which component can be used to solidify the liquid components of the product when all are heated together, then cooled to room temperature. This definition includes waxes in the traditional sense, i.e., those plant, animal or mineral waxes containing primarily esters of higher fatty acids and alcohols, free higher acids and alcohols, and saturated hydrocarbons; examples of such traditional waxes include, but are not limited to, carnauba wax, candelilla wax, beeswax, synthetic wax, shellac wax, spermaceti, lanolin wax, ozokerite, bran wax, ceresin wax, bayberry wax, paraffin, rice wax and jojoba wax. However, it also includes other non-traditional wax-like materials, including, but not limited to, various fatty alcohols, fatty acids, fatty esters, polyethylenes, polyethylene glycols, and sterols as well as synthetic resinous products having a wax-like, i.e., hard, brittle, relatively non-greasy, texture, such as silicone waxes.

The wax based product will also comprise one or more oils or oil-like emollients. Any cosmetically or pharmaceutically acceptable oil may be used in the wax base, the selection only being limited by the necessity for successfully wetting out pigments, a technique well known in the art. Examples of suitable oils or oil-like emollients can be found in the International Cosmetic Ingredient Handbook, CTFA, 1996, the contents of which are incorporated herein by reference. Useful materials include, but are not limited to, castor oil, coconut oil, corn oil, jojoba oil, cottonseed oil, soybean oil, walnut oil, wheat germ oil, sunflower seed oil, palm kernel oil, calendula oil, C8–18 triglycerides, lanolin and lanolin derivatives, illipe butter, shea butter; esters, such as isodecyl neopentanoate, tridecyl octanoate, diisostearyl malate, cetyl palmitate, cetyl octanoate, cetyl stearate, cetyl myristate, isopropyl palmitate, isopropyl myristate, dipentaerythrityl hexahydroxy stearate/stearate/rosinate, polyglyceryl-2-isostearate, neopentyl glycol distearate, isodecyl oleate, decyl isostearate, diisopropyl sebacate, PEG-4 diheptanoate, dioctyl malate, and isohexyl neopentanoate; fatty alcohols, such as lanolin alcohol or oleyl alcohol; and silicone oils, such as cyclomethicone, dimethicone, cetyl dimethicone, lauryl trimethicone, and dimethiconol. The oil component comprises from about 20–70%, more preferably about 50–70%, of the total weight of the wax-based product. Preferred formulations contain a combination of at least one oil in an amount of about 15–40%, a C8–C18 triglyceride in an amount of from about 5 to about 20%, at least one ester, preferably at least two esters, each in an amount of about 1 to about 10%, more preferably about 2 to about 8%, and a synthetic wax in an amount of about 1 to about 10%.

The invention is further illustrated by the following non-limiting examples.

EXAMPLES

Example 1

This illustrates a lipstick prepared in accordance with the present invention.

| Material | Weight percent |
| --- | --- |
| Castor oil | 29.60 |
| Sorbitan sesquioleate | 1.20 |
| Wax base* | 42.00 |
| Pigment grind** | 7.20 |
| Shadow pigment | 10.00 |
| Blue interference pigment | 10.00 |

*containing diisostearyl malate, caprylic/capric triglyceride, oleyl oleate, polydecene, synthetic wax, candelilla wax, carnauba wax, ozokerite, beeswax, dipentaertythrityl hexahydroxystearate/stearate/rosinate, isodecyl neopentanoate
**containing castor oil, organic pigments, barium sulfate, and iron oxides (total pigments <2%)

The pigment grind is made according to standard procedures, e.g., triple roller milled. All waxes and oils are melted together, and kept at about 80–90° C. To the molten mass is added the pigment grind, then the shadow pigment and interference pigment. The mixture is blended until the pigments are distributed homogeneously, and then poured into a mold and allowed to cool.

What we claim is:

1. A cosmetic composition containing from about 1 to about 20% of a four-layered interference pigment comprising an innermost layer of mica, a first outer layer of metallic oxide, a second outer transparent layer of silica, and an outermost layer of metallic oxide, combined with about 1 to about 20% of a traditional interference pigment.

2. The composition of claim 1 in which the metallic oxide-containing layers comprise at least one iron oxide.

3. The composition of claim 1 in which the first outer layer comprises an iron oxide, and the outermost layer comprises an iron oxide and titanium dioxide.

4. The composition of claim 1 in which the traditional interference pigment exhibits a green, violet, gold or blue color.

5. The composition of claim 1 containing a red-orange four-layered interference pigment comprising an innermost layer of mica, a first outer layer of iron oxide, a second outer transparent layer of silica, and an outermost layer of iron oxide and titanium dioxide, combined with a traditional interference pigment which exhibits a green, violet, gold or blue color.

6. The composition of claim 5 in which the traditional interference pigment is one having a white base with a colored pearlescence.

7. The composition of claim 5 in which the four-layered pigment and the traditional interference pigment are each present in an amount of about 5 to about 15%, and the amount of each is approximately equal.

8. The composition of claim 1 which is a wax-based product.

9. The composition of claim 5 which is a wax-based product.

10. The composition of claim 7 which is a wax-based product.

11. A method for enhancing the dimensionality of a facial or body feature which comprises applying to the feature a composition of claim 1.

12. A method for enhancing the dimensionality of a facial or body feature which comprises applying to the feature a composition of claim 5.

13. A method for enhancing the dimensionality of the lips which comprises applying to the lips a lip product comprising the composition of claim 8.

14. A method of enhancing dimensionality of the lips which comprises applying to the lips a composition of claim 9.

15. A method of enhancing dimensionality of the lips which comprises applying to the lips a composition of claim 10.

16. The composition of claim 1 in which at least one of the pigment layers comprises an organic pigment.

17. The composition of claim 1 in which the traditional interference pigment is one having a white base with either a colored or colorless pearlescence.

18. The composition of claim 1 in which the traditional interference pigment is one having a colored base with either a colored or colorless pearlescence.

19. The composition of claim 1 in which the four-layered interference pigment comprises layers in the ratio of about 61:15:9:(14.3+0.7) mica:iron oxide:silica:(titanium dioxide+iron.

* * * * *